United States Patent [19]
Kambara et al.

[11] Patent Number: 5,824,481
[45] Date of Patent: *Oct. 20, 1998

[54] DNA ANALYZING METHOD

[75] Inventors: Hideki Kambara, Hachiouji; Kazunori Okano, Shiki; Satoshi Takahashi, Kunitachi; Keiichi Nagai, Higashiyamato; Kazuko Kawamoto; Hiroko Furuyama, both of Kokubunji, all of Japan

[73] Assignee: Hitachi, Ltd., Tokyo, Japan

[ * ] Notice: The term of this patent shall not extend beyond the expiration date of Pat. No. 5,650,274.

[21] Appl. No.: 812,698

[22] Filed: Mar. 6, 1997

Related U.S. Application Data

[63] Continuation of Ser. No. 263,663, Jun. 22, 1994, Pat. No. 5,650,274.

[30] Foreign Application Priority Data

Jul. 25, 1993 [JP] Japan ..................................... 5-155534
Jul. 30, 1993 [JP] Japan ..................................... 5-189624

[51] Int. Cl.$^6$ ..................................................... C12Q 1/68
[52] U.S. Cl. ................................... 435/6; 935/77; 935/78
[58] Field of Search .............................. 422/82.01, 68.1, 422/50, 52, 55, 57, 82.09; 435/6, 91.2, 174, 287.2, 288.7, 181, 239, 820, 283.1, 287.1, 288.1, 288.2, 289.1, 290.1, 290.4; 935/87; 536/23.1, 24.3–24.33

[56] References Cited

U.S. PATENT DOCUMENTS 5,650,274  7/1997  Kambara et al. ........................... 435/6

FOREIGN PATENT DOCUMENTS 0534858  3/1993  European Pat. Off. .

*Primary Examiner*—Lisa B. Arthur
*Assistant Examiner*—Jehanne Souaya
*Attorney, Agent, or Firm*—Antonelli, Terry, Stout & Kraus, LLP

[57] ABSTRACT

A DNA analyzing method which bonds a first oligomer of known base sequence to a DNA fragment obtained by digesting a DNA sample with a restrictive enzyme. The oligomer and DNA fragment are hybridized to other oligomers which have the sequences of all combinations of the types of bases within the length of several bases following the known base sequence. The presence or absence of hybridization or complementary DNA strand extension is determined and identifies the DNA fragment terminal sequence from this result. The DNA fragments are then fractionated and analyzed to determine the sequence. This DNA analyzing method provides an effective analysis of mixtures of long DNAs or DNA fragments.

2 Claims, 7 Drawing Sheets

DNA ANALYZING METHOD

CROSS-REFERENCE TO RELATED APPLICATION

This application is a continuation application of application Ser. No. 08/263,663, filed on Jun. 22, 1994, now U.S. Pat. No. 5,650,274, issued on Aug. 5, 1997.

BACKGROUND OF THE INVENTION

The present invention relates to a DNA analyzing method including DNA sequencing.

Conventional DNA sequencing of large segments of DNA (e.g. $10^5$ to $10^6$ (100K to 1M) base length) requires subcloning processes. During such subcloning processes, the target DNA is digested with restriction enzymes to produce fragments of the target DNA. The fragments are cloned in a plasmid, which is used as a vector in the cloning process. *E. coli* transformed with the plasmid is cultured in the agar thereafter. As only transformed *E. coli* can survive and form colonies in the agar, we can select *E. coli* transformed by the plasmid by picking the colonies. Then the target DNA fragments subcloned in the plasmid are isolated from *E. coli* and the isolated target DNA fragments are sequenced. The target DNA fragments are then separated by picking obtained colonies or clones and DNA sequencing carried out for each clone of the plasmid containing the isolated DNA fragment. Normally, 300 to 500 DNA bases can be determined by one sequencing operation, and sequencing of 1 mega ($10^6$) base requires analysis of 2000 or more colonies. Furthermore, colonies containing the same DNA fragments may be selected for the analysis; this requires colonies in the number of several times 2,000, namely, close to 10,000 colonies to be selected for analysis.

According to conventional methods, base sequencing of the human genome and other organisms requires digesting of a great length of DNA by restriction enzymes and subcloning the digested DNA into vectors such as plasmid and yeast chromosomes, transforming an appropriate host cell with said plasmids of yeast chromosomes thereby forming a colony derived from one clone containing a single DNA digested product and selecting each DNA fragment by picking the colony. Then DNA fragments are amplified by culturing microbes obtained from each colony to provide a large amounts of the DNA fragment required for base sequencing techniques. Called "cloning or subcloning", this biological technique has disadvantages of taking a lot of time for culturing and is not suitable for automation. Such conventional techniques are discussed in Molecular Cloning, A Laboratory Manual (2nd Version) (Chapters 1 to 4 and Chapter 9, Cold spring Harbor Laboratory Press, 1989).

According to the above techniques, single DNA fragment species required for sequencing are prepared using vectors and transformed colibacillus and yeast requiring the use of a special P2 facility. Another disadvantage of the method is the amount of time required to culture the microbes and pick large numbers of colonies for analysis, making the method unfit for automation.

Primer Walking (Science, Vol. 258, pages 1787 to 1791, 1992) is known as a method for analysis of long DNA fragments; it provides for sequencing of 40 DNA bases from one end of a fragment using a first primer. A second sequencing step is carried out with a second primer which is an oligomer having a sequence in the vicinity of the first sequenced DNA terminal. sequencing is carried out step by step using new primers which have sequences complementary to the sequenced DNA. Analysis of 1 megabase of DNA requires 2500 sequencing steps with this method and each analysis requires one or more days; thus several years have been required for all analyses.

Thus, such large scale DNA sequencing methods comprise processes requiring much cost and time. Depending on the sizes and types of the DNA fragments digested by restriction enzymes, some of the DNA fragments have been difficult to introduce into vectors by cloning. Consequently, large scale DNA sequencing has been a problem requiring the development of a new technique.

SUMMARY OF THE INVENTION

The object of the present invention is to provide solutions to the problems of said conventional sequencing techniques and a DNA analysis method ensuring effective analysis of long DNA fragments or mixtures of DNA fragments. Another object of the present invention is to provide a method which allows DNA sequencing without cloning and permits automatic amplification and selection of DNAs.

To achieve said objectives, the DNA analysis according to the present invention comprises:

(1) a process of digesting a long DNA fragment at a certain sequence portion using an enzyme or the like and ligating the DNA, which is labeled with a fluorophore or the like, with a DNA oligomer which has known sequence, to the digested portion of the DNA fragments with the termini;

(2) a process of forming single stranded DNA at least in the vicinity of the terminal of the double strand, (3) a process of separating DNA according to the difference of the terminal sequences following the ligated known oligomer sequence and, (4) a process of fractionating and sequencing the separated DNA.

The present invention provides a DNA analyzing method comprising introducing a known sequence at the terminal of a DNA fragment by a connecting oligomer, and a process of sequencing the specific DNA fragment alone which has certain base sequences (2 mer to 6 mer) immediately connecting oligomer DNA sequence at the terminal of this DNA fragment.

Figure 2:
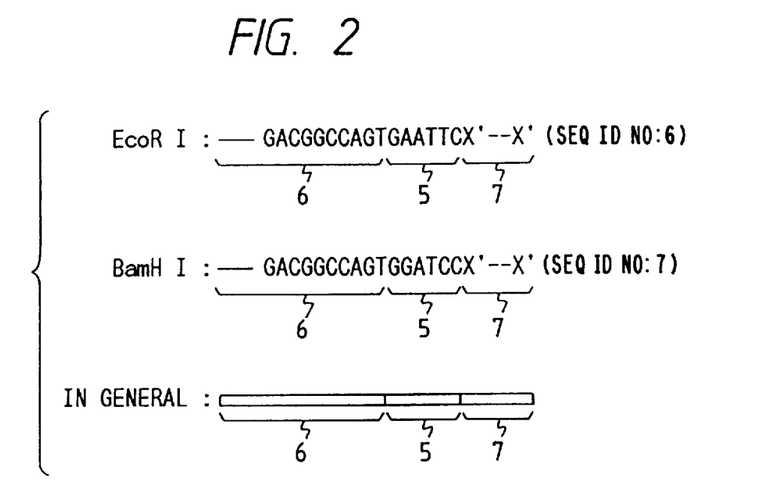
FIG. 2 is a structure diagram representing the base sequence of the DNA probe used in one embodiment of the present invention.

The DNA is digested by a restriction enzyme having the property of recognizing and digesting a certain sequence. The restriction enzyme used in the present case can be any enzyme; Hind III and Not I are used for example. The terminal base of the DNA fragment can be labeled with a fluorophore or the like to ensure that many types of the generated DNA fragments can be easily separated and isolated (FIG. 2). Fluorophores such as FITC (fluorescein isothiocyanate having an emission wavelength of 525 nm) and TEXAS RED (sulforhodamine 101 having an emission wavelength of 613 nm), chemical luminescence or radiolabels may be used as labels. Many fragment species are produced through the digestion. As too many DNA species are not good for amplification of DNA fragments by PCR, the DNA fragments are separated by gel electrophoresis to be fractionated before the PCR amplification. This separation may not be very complete and a fraction can contain several DNA fragment species. In addition to gel electrophoresis, DNA probe arrays, liquid chromatography or affinity chromatography can be used as the separation means. When the amount of DNA fragments is not sufficient for DNA sequencing, the number of DNA fragment copies can be amplified by repeated DNA polymerase reactions (PCR amplification) using the ligated known oligomer sequences at both ends of DNA fragments.

The DNA fragments obtained at this stage are composed of several species of DNA fragments; one specific DNA fragment species is separated in a more complete manner to determine the base sequence and selective base sequencing performed. Said selective base sequencing will be done in the following procedure:

The oligonucleotide has a base sequence comprising the known DNA sequence complementary to the oligonucleotide ligated to the portion digested by the restriction enzyme and additional 2- to 6-base sequence at its 3' terminal. This oligonucleotide hybridizes to the ligated oligomer and 2- to 6- base sequence immediately adjacent to the digested portion of DNA fragments and is added to the mixture of several species of DNA fragments as a primer, so that the primer will hybridize to the 3' terminal of the specific DNA fragments. Only the specific template DNA is selected to undergo complementary DNA strand extension in the presence of four bases of adenine (A), thymine (T), guanine (G), cytosine (C), ddATP, ddTTP, ddGTP, and ddCTP, and DNA polymerase; then the sequencing reaction products are used for selective sequencing. Each DNA fragment species where 3' terminals of the hybridized strand obtained comprise adenine, thymine, guanine, cytosine is analyzed by electrophoresis to determine DNA fragment length and base sequence. Furthermore, to enhance selectivity of the said primer, complementary DNA strand extension can be carried out at the temperature of 60 degrees Celsius or more where primer binding performance is reduced and only perfectly hybridized primers can work. This is because hybridization between said primer and DNA fragments is provided by hydrogen bonding, so when reaction the temperature is increased, stability is maintained at the 3' terminal sequence portion of the primer only for the fragments having sequences having perfect complementarity and, in other fragments, complementary DNA strand extension does not take place over that temperature. Therefore, when the hybridization reaction temperature (annealing temperature) is raised to 60 degrees Celsius or more, more effective selection will be ensured, thereby providing effective selectivity.

Figure 6:
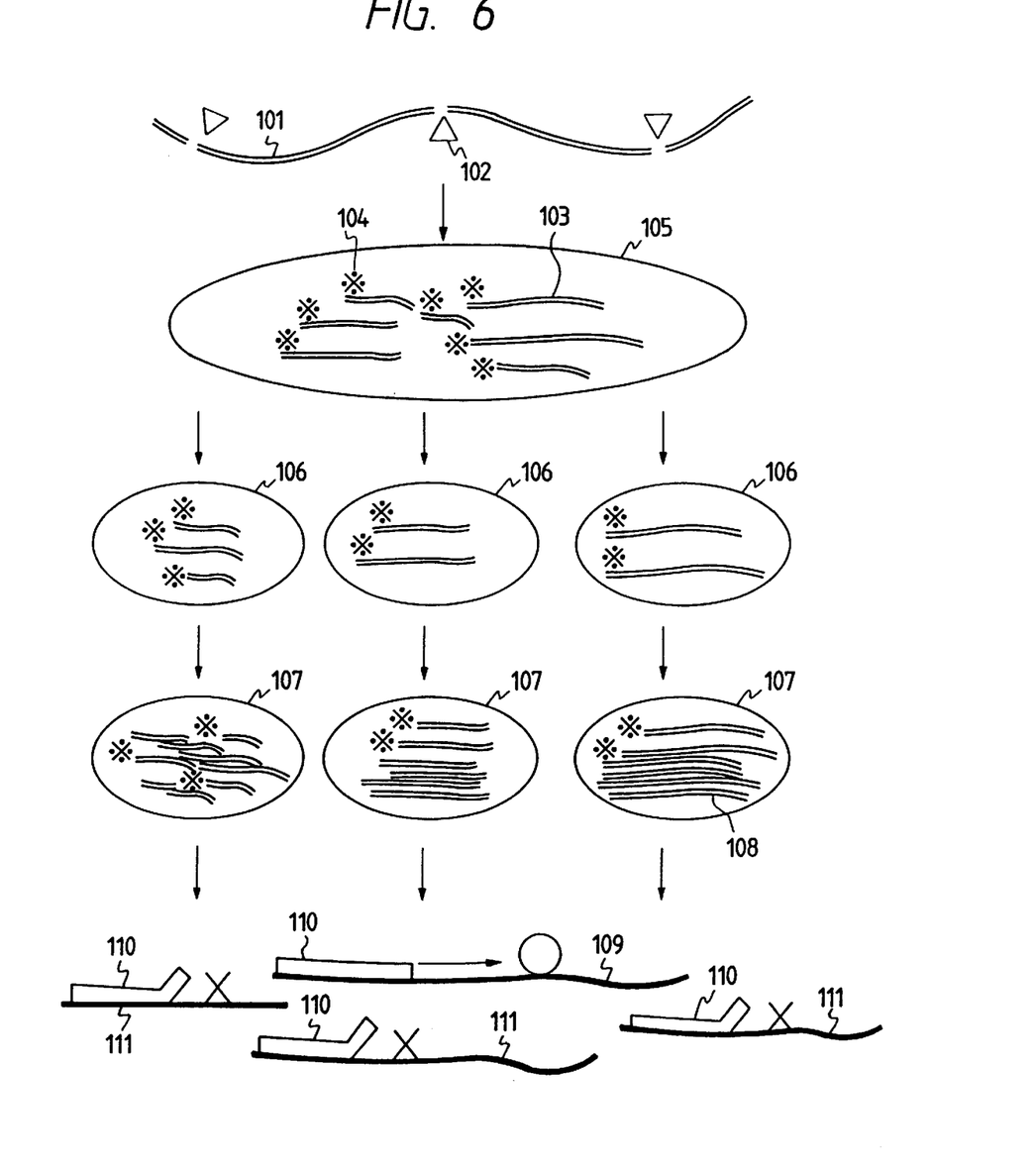
FIG. 6 is a flow diagram representing the DNA analyzing method in another embodiment of the present invention.
Figure 10A:
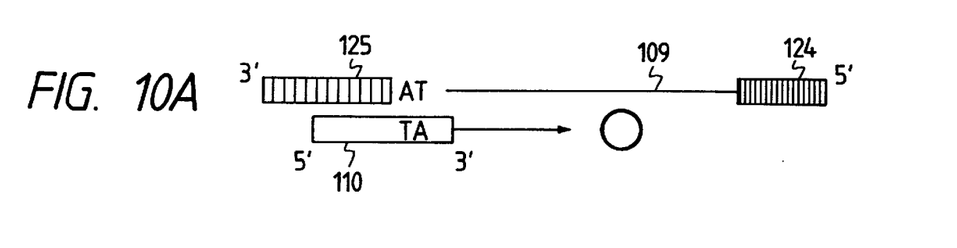
FIGS. 10A and 10B are schematic illustrations to show the selective base sequencing method in another embodiment of the present invention.
Figure 10B:
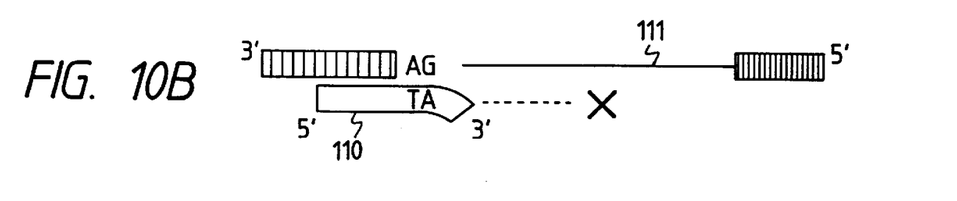

The following discusses the principle of said selective DNA sequencing according to FIGS. 6, 10A and 10B. In the DNA sequencing operation, in the final process of FIG. 6, many kinds of template DNAs 109 or 111 and one type of primer 110 are mixed to cause hybridization, and only the template DNAs 109 capable of complete hybridization with primer 110 are sequenced. In greater detail, DNA fragment group 107 which comprises of five to six species of DNA fragments in FIG. 6 is the double stranded DNA comprising the known DNA oligomer sequence portion connected to the restriction enzyme digested portion at both terminals and the unknown DNA sequence portion at the center. These DNA fragments are heated and changed into single stranded DNA 109 and 111 in FIGS. 10A and 10B, and are hybridized with the primer 110 comprising the sequence complementary to the known sequence portion at the terminus and the base sequence complementary to two bases at the 5' terminal of the unknown sequence portion (the portion where two bases at the 3' terminal of the primer will be bonded) following it. Two bases on the terminal side of the DNA fragment followed by the known sequence portion of ligated oligomers 109 and 111 are unknown bases, and the sequence differs according to the species of the DNA fragments. Therefore, the type of the primer capable of complete hybridization differs depending on the species of the DNA. This example is illustrated by a case of a primer having the known sequence and the additional two bases, however the additional two bases can be increased up to 6 bases. The number of primer types depends on the additional number of bases. It is 16 for two bases and $4^6$ for six bases. When the number of template DNA (or DNA fragment to be analyzed) species is much less than the number of primer types, the possibility of one primer hybridizing to more than two template DNA species is very low. This means that only one type of DNA fragments (FIG. 10A) is subject to hybridization with one type of primer, so only one type of DNA sequence can be read, analyzed and determined on a selective basis. It should be noted, however, that the length of the primer which hybridizes with the known DNA sequence portion at the 5' terminal and the additional several bases following it must be more than six bases for the primer to function. A primer longer than 16 mer is preferred from the viewpoint of stability. The length of primer can be adjusted by changing the length of oligomer ligated at the DNA fragment terminus.

Enzyme digestion and ligation of the oligomer having a known sequence allows the known DNA sequence to be introduced at both termini of the unknown DNA fragments. The introduction of labels onto DNA fragments facilitates separation and fractionation of the DNA fragments. After separation and fractionation, five to six or less DNA fragment species are contained in each fraction. A small number of DNA fragment species in a fraction facilitates DNA sequencing on a selective basis. The fractionated DNA fragments contain the unknown sequences between the known sequences of the ligated oligomers, and can be amplified enzymatically by the extensively used PCR method. The primer containing the oligomer sequence and the additional sequence of up to two to six bases is used for complementary DNA strand extension on a selective basis, where only the specific DNA, to which the additional sequence of the primer can hybridize perfectly are amplified and read out. Selectivity of the complementary strand extension depends on temperature; the selectivity of the amplification of a special DNA fragment species can be improved by raising the reaction temperature over 60 degrees Celsius.

For separation and fractionation of DNA fragments by their sequence differences, it is also possible to use the features of the DNA strand undergoing hybridization with the DNA strand having the complementary sequence. Various types of DNA oligomers are immobilized to a solid surface according to their sequence so that the target DNA fragments are hybridized with it. The oligomers have the sequences complementary to the ligated oligomers at the DNA fragments and the additional two to six bases at the 3' terminus. When the number of additional bases is two, the number of oligomer species becomes 16 according to the sequence variation of the additional two bases. The oligomers are immobilized on the solid support separated by their additional sequences. Since the target DNAs are double stranded DNAs, they are converted into single stranded DNAs by alkali denaturation, or are partially digested from the double strand 3' terminal using such enzymes as exonuclease III, to be made into single strands with a 5' terminal overhang. Alternatively, these DNAs are digested from the 5' terminal by λ exonuclease, so that the terminal has a 3' terminal overhang; after that, they are hybridized with various types of DNA oligomers immobilized on the solid surface, thereby separating the target DNAs. These target DNAs are partially separated according to the type of said DNA oligomers, to determine the sequence. This process is concurrently implemented for various types of DNA fragments.

To sum up, the oligomer of the known sequence is ligated to the terminal of the DNA fragment obtained by digesting the sample with the restriction enzyme, and hybridization allowed to occur between the oligomer and DNA fragment and using the DNA probe chip whose solid surface is fixed with the oligomers having the combinations of sequences for many of the base sequences (all of them if possible) within the length of the additional base sequence following the known sequence. Furthermore, fractionation of DNA fragments is possible after hybridization between probes and DNA fragments has occurred so that extension by DNA polymerase will proceed only where probes are completely hybridized with DNA fragments to improve the stability of the hybrids. Detection is made to find out whether hybridization has occurred in a cell on the solid surface of the chip or not, and the terminal sequence of the DNA fragments determined from the address of the cells in which DNA fragments are held by hybridization; then the individual DNA fragments are removed from the surface to be analyzed. This procedure provides a method of effective analysis of mixtures of long segments of various DNA fragments which is applicable to the simultaneous analysis of a great number of the DNA fragment species having different sequences.

Direct sequencing of long DNA segments reaching 1 megabase is very difficult. So the major point of the present invention is to provide a means of completing analyses in a short period of time by parallel sequencing of DNA fragments produced by enzymatic digestion and separated after said digestion. When a restriction enzyme recognizing six bases is used, the average DNA fragment length is several thousands of base. The number of DNA fragment species is about 100. Since the terminal of each DNA fragment has an inherent sequence, separation is possible by recognizing and hybridizing it with a complementary sequence. For stable hybridization a length of complementary sequence of 10 mer or more is required. The number of oligomer species comprising ten mer is $4^{10}$, i.e., about $10^6$, so it is not easy to make and prepare all of these oligomer species. Several hundreds of DNA fragment species are present in the digestion product of 1 Mb DNA; therefore, several thousands of oligomers are required to recognizeand hybridize said species. Namely, their identification is possible by using oligomers of five to six mer as an identification region. It is possible to create the DNA probes capable of complementary hybridization, having sufficient stability with the target DNA if the DNA probes contain said sequence of 5–6 mer for identification and the sequence of the portion digested by the restriction enzyme as well as part or all of the known sequence ligated to the terminal. The target DNA in a solution can be retained and separated according to the base sequences in the identification region of the DNAs which make the complementary hydrogen bonds with DNA probes, by pouring the solution, including target DNAs, onto the solid surface where these various types of DNA probe are immobilized. The separated DNA undergoes parallel sequencing reactions and can be analyzed. When the number of DNA fragment species in a mixture is less than 100, the length of the identification region in the probes can be three to four mer.

DESCRIPTION OF THE PREFERRED EMBODIMENTS

EMBODIMENT 1

Figure 1:
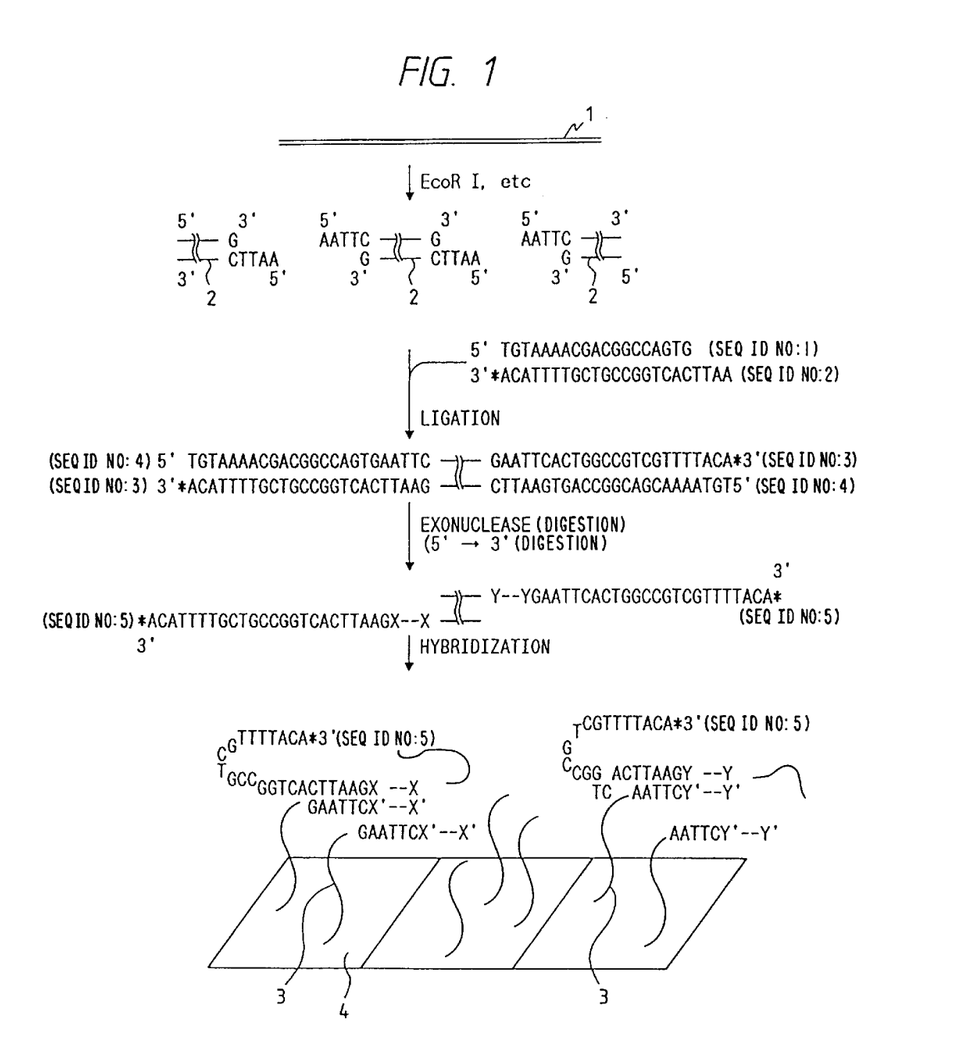
FIG. 1 is a flow diagram representing the DNA analyzing method in one embodiment of the present invention.

The present embodiment will be described with reference to Figures. The following describes the example using γ phage DNA having 48,000 bases as one double stranded DNA sample 1 to be analyzed: The γ phage DNA is digested by the restriction enzyme EcoRI (G↓ATTC: restriction enzyme EcoRI recognizes the base sequence GAATTC and cuts between G and A: this description applies to all the following examples), and ethanol precipitation is utilized for purifying digested DNA. The double stranded oligomer, with a 5' overhang sequence 5'-AATT-3' and double stranded portion has the following sequence:

TGTAAAACGACGGCCAGTG SEQ ID NO:1
CATTTTGCTGCCGGTCACTTAA SEQ ID NO:2 and is ligated to the digested portion by using the enzyme ligase. In FIG. 1, "2" denotes the unknown sequence portion within the DNA fragment while "*" denotes the fluorophore label. As shown in FIG. 1, the DNA fragment with the 3' terminal sequence of *ACATTTTGCTGCCGGT-CACTTAAG SEQ ID NO:3 . . . is generated from the ligation of SEQ ID NO:2 to the DNA fragment. In the case of γ phage DNA, the number of the digested fragments generated by the restriction enzyme EcoRI is as small as five. The sample is similarly digested with BamH I (G GATCC), Bal I (TGG CCA), BapH I (T CATGA), and the oligomers having known sequence are ligated to the terminal of the DNA fragments. The area in the vicinity of the 3' terminal of this oligomer is labeled with a fluorophore or a ruthenium complex which is an electroluminescence reagent. A radioisotope label may also be used. In the present invention, TEXAS RED (trademark of Molecular Probe Co.; having a maximum fluorescence emission wavelength of about 615 nm) was used as the label. After the enzymatic digestion and ligation process, almost 40 fragments of γ DNAs were produced. Exonuclease is added to these reaction products to digest DNA fragment from the 5' terminal. After they are turned into DNA fragments having 3' overhangs, the DNAs are separated by the ethanol precipitation and are suspended in the 1×TBE buffer of 10 µl (10 microliters).

Probe chip 4 is created by bonding various types of oligonucleotides (DNA oligomer probe 3) at pitches of 0.1 mm on the glass surface measuring 6 mm×10 mm in the same way as disclosed in the document (Science Vol. 251, pages 766 through 772, 1991). A total of 6,000 separated cells are formed on probe chip 4. FIG. 2 shows the structure of the DNA probe used in this embodiment of the present invention. The DNA probe has the enzyme recognition sequence 5 (restriction sites), the universal primer portion of 6 being a common sequence among the DNA probes. Specific hybridization of the addition sequence portion is determined as a means of recognizing and separating the sample DNA sequence. As illustrated in FIG. 2, oligomers (15 mer–20 mer) SEQ ID NO:6 and SEQ ID NO:7 of 1024 species ($4^5$), which include the restriction site sequences of 6 mer (the variation of restriction site sequence is four in this case because four types of restriction enzymes are used) and the selective sequence portion 7 of 5 mer in the unknown region (x'. . . x') of the DNA fragment (the variation of the sequence is $4^5$=1024 and this region is used to identify and select DNA fragments), are bonded on the glass surface with different oligomer species for each cell of probe chip 4 (also referred to as array sensor). The length of the selective sequence portion 7 was assumed as 5 mer; it can be 2 to 6 mer. If the selective sequence portion 7 is too short, various species of DNA fragments will be hybridized in one cell. Conversely, if the selective sequence portion 7 is too long, the required oligomer species will increase in number, resulting in difficulties in the fabrication of the said probe chip. When fragments are separated by electrophoresis in advance, the length of the selective sequence portion 7 can be about 2 men. In order to investigate whether complete hybridization at the sequence portion of the 2 mer has been achieved or not, complementary DNA strand extension (this reaction is sensitive to two bases at the 3' terminal) is performed to improve the stability as the hybrid, thereby distinguishing it from the hybrid which was not extended.

Figure 3:
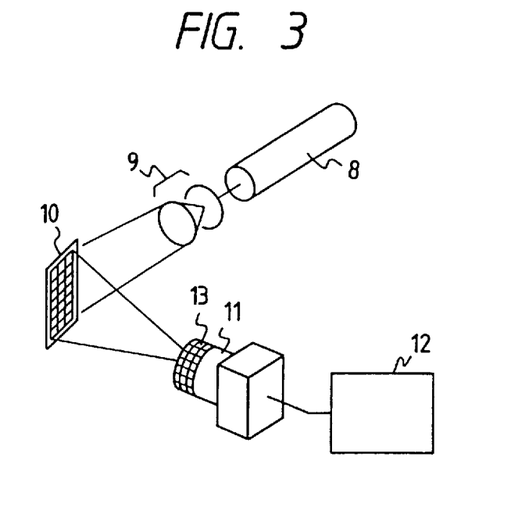
FIG. 3 is a schematic illustration to describe the instrument used to measure the presence or absence of hybridization reactions used in one embodiment of the present invention.
Figure 4:
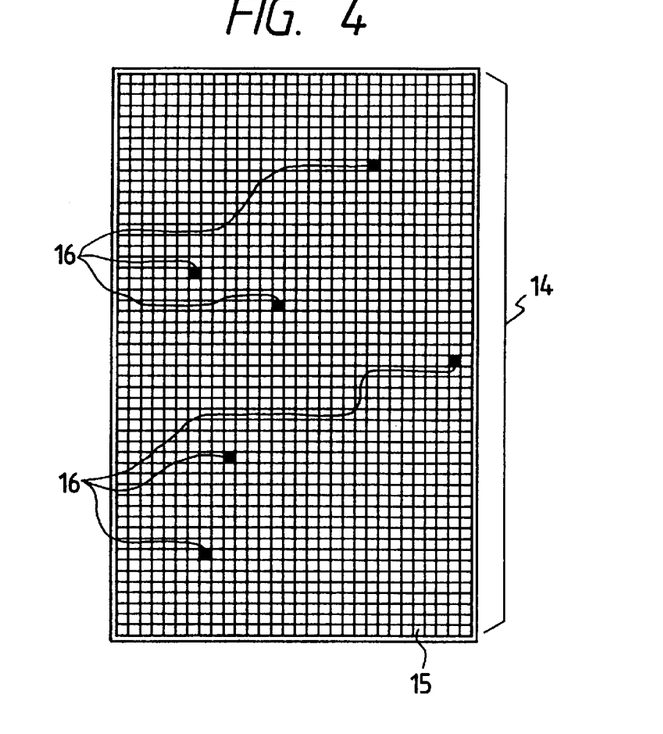
FIG. 4 is a view showing the fluorescence image pattern resulting from DNA fragments hybridized on the probe chip used in one embodiment of the present invention.

The liquid containing DNA is injected on the probe chip, and DNA fragment is hybridized with the oligomer on the probe chip. It is held at the temperature of 37 degrees Celsius for about one hour to allow sufficient hybridization; then it is washed with 1×TBE buffer solution. The state of hybridization on the probe chip is measured by the instrumentation system given in FIG. 3. The probe chip 10 is irradiated by laser 8 (YAG laser, oscillation wavelength of 532 nm and output of 10 mW) through collimator lens 9, and the fluorescence image on probe chip 10 is observed by highly sensitive 2-dimensional camera 11 provided with filter 13. The similar measurement is possible by narrowing the laser beam and using the laser microscope which scans the probe chip range. In FIG. 3, "12" denotes data processor. FIG. 4 shows an example of the observed fluorescence image schematically. Various DNA probes are immobilized on cells in the pro-be array 14. Fluorescent light is observed only from cell 16 where the target DNA fragment is contained. As each cell 15 contains one probe species, the terminal base sequence can be identified from the cell position where fluorescence is emitted. It is also possible to fractionate and isolate the DNA trapped in the cell. Fractionation of the DNA from each cell can be performed based on the invention disclosed in Japanese Patent Application Laid-open NO.5-236997 (Application No. 4-42829 "Polynucleotide Capturing Tip": the corresponding patent application in U.S. is U.S. patent application Ser. No. 08/021,667 U.S. Pat. No. 5,434,049).

When fractionation of a large number of DNA copies is desired, magnetic beads (fine iron particles whose surface are coated with the organic substance to permit DNA bonding) of which retains a DNA oligomer having the same sequence as that on each cell on the surface thereof are put into the sample tube, thereby causing hybridization of DNA with the oligomer on the beads followed by separating by taking out the beads with DNA using a magnet. This procedure should be repeated.

Figure 5:
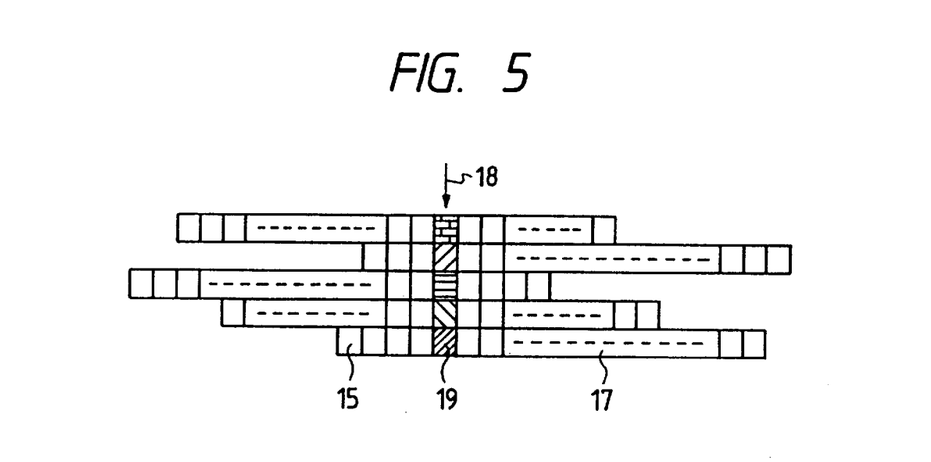
FIG. 5 is a schematic illustration to describe other probes (combinations of linear probe arrays) used in one embodiment of the present invention.

Alternatively, fractionation method as shown in FIG. 5 is also available. This technique used a plurality of linear DNA probe array comprising thin plates. Each probe array has many cells holding different oligomer probes, respectively, however, only one cell per array is used to fractionate DNA at a time. Each probe array can be separated for fractionating the DNA held in the cell. For this purpose, one or more of these chips are prepared and are laid out superimposed by shifting the position of more than one liner DNA probe array 17 to the direction where separated cells are laid out. The flow channel 18 for sample solution is formed so that the separated cell, where the probe corresponding to the DNA fragments to be fractionated on the specific line is fixed (DNA probe cell 19 to capture the target DNA), will be arranged in one line. Hybridization is made by pouring the sample solution into flow channel 18 and more than one target DNA can be in sequence captured, thereby ensuring effective fractionation.

The probe sequences to be used are selected by shifting the position of the chips, as shown in FIG. 5. After the hybridization and capturing of DNA fragments on the chips, each chip is separated and specific DNA fragments are recovered separately. Different DNA fragments can be captured by shifting chips superimposed on each other.

It is also possible to use the following steps: Various types of probe rods with DNA oligomer probes mounted on the slender bar tip of the rods are prepared to select the probe rods having the required sequence. These rods are bundled and put into the sample solution, thereby causing hybridization and separation of the DNA. This means that the probe holding medium, such as rods which can be separated from each other, can be used in place of the sheet containing cells holding various probes on them. In this case, when selecting probe rods where the probe corresponding to the DNA fragment are fixed, the two-dimensional probe array composed of more than one linear DNA probe array 17 arranged in two dimensions is analyzed and inspected in advance, using the device as described with reference to FIGS. 3 and 4 before fractionation of the DNA fragment. The DNA with the known terminal sequence can be singly separated with this method. When the DNA length is 1 to 2 kb or less, the number of sample DNA copies can be amplified by PCR (Polymerase Chain Reaction); therefore, DNA can be separated and amplified directly from probe chips 4 and 10, and probe arrays 14 and 17, or PCR amplification can be performed directly on the probe chips 4 and 10, and probe arrays 14 and 17 by installing a barrier to partition the sample holding cells from other cells on these chips and arrays. For the PCR primer, it is possible to use the complementary oligomer on both terminals including the known sequence. When the probe comprising the DNA oligomers on the probe chip is hybridized with the sample DNA at its 3' terminal side, and complementary DNA strand extension is possible from the probe oligomer 3' terminal side along the sample DNA strand, then the complementary strand is formed on the probe chip first and can be used as a template for PCR amplification. In this case, the same strand as that of the sample DNA is separated by thermal denaturation, and is used for analysis such as sequencing.

DNA sequencing reactions with the fractionated DNA fragment are conducted according to known procedures, and DNA sequence is determined by gel electrophoresis or other means. Since the sequence portion common to the oligomers ligated to the DNA can be used as sequencing primers, this eliminates the need for preparing many types of primers. Sequencing reactions and operations (by gel electrophoresis) can be performed for many samples at one time. If long DNA segments are digested and separated by the present invention, these separated samples can be sequenced at one time. If fragmentation of the sample by restriction enzyme is repeated several times by the enzymes with different combinations of restriction enzymes, all the sequences can be determined exhaustively. Furthermore, if one round of sequencing is not sufficient to sequence the required length of DNA, the new primer is synthesized in the vicinity of the terminal of the DNA sequence read out, and the sequence of a still longer portion is determined.

In the embodiment discussed above, the target DNA is classified and separated according to the 5-mer base sequence immediately adjacent the portion digested by enzyme. When there are only a few types of the target DNA fragments, classification and separation are possible by two to four mer base sequence. When there are many types of the fragments, they are fractionated roughly into 10 fractions by gel electrophoresis; then the oligomer having a short sequence for classification of each group can be used for analysis and inspection.

In the embodiment discussed above, the DNA made to have single strands by exonuclease digestion is obtained after hybridization. It is also possible to obtain the target DNA by hybridization after single strands have separated by thermal denaturation. Furthermore, the DNA fragments immobilized on the glass support can be obtained by complementary DNA strand extension reaction and thermal denaturation, and can be used for sequencing analysis. Furthermore, PCR amplification can be performed using primer (DNA oligomer probe) and immobilized on the solid surface under this condition, as well as the universal primer, thereby increasing the number of copies to be used for analysis.

EMBODIMENT 2

Figures 7A, 7B:
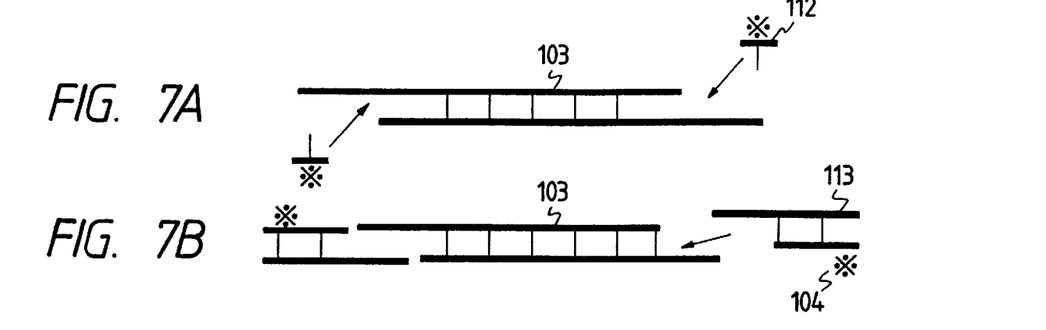
FIGS. 7A and 7B are schematic illustrations to describe the labeling of DNA fragments with a fluorophore.

Another embodiment of the present invention will be described with reference to FIGS. 6 through 11. FIG. 6 represents the flow of the new sample handling for DNA sequencing method, while FIGS. 7A and 7B through 11 provide detailed illustrations of the techniques in each process. The DNA 101 to be sequenced and analyzed is digested by the restriction enzyme (Hind III) 102 which recognizes and digests specific sequences. This operation generates DNA fragment group 103 with its terminal base sequenced. Whenever required, this DNA fragment terminal base is labeled with fluorophore 104 in the method shown in FIGS. 7A and 7B. (1) in FIG. 7A denotes the method of incorporating the monomer 112 of DNA labeled with a fluorophore into the terminal of the DNA fragment 103, using the polymerases. FITC (fluoresceine isothiocyanate having an emission wavelength of 525 nm) is used as the label of DNA base 112. FIG. 7B shows the method of bonding the short DNA 113 having the overhang which can be bonded with the overhang portion of one strand of the terminal digested by restriction enzyme 102, by means of an enzyme such as ligase. The short DNA fragment 113 is labeled with fluorophore 104 in advance through amino residue or the like. Texas Red (sulforhodamine 101; having an emission wavelength of 613 nm) is used as the label.

Figure 8:
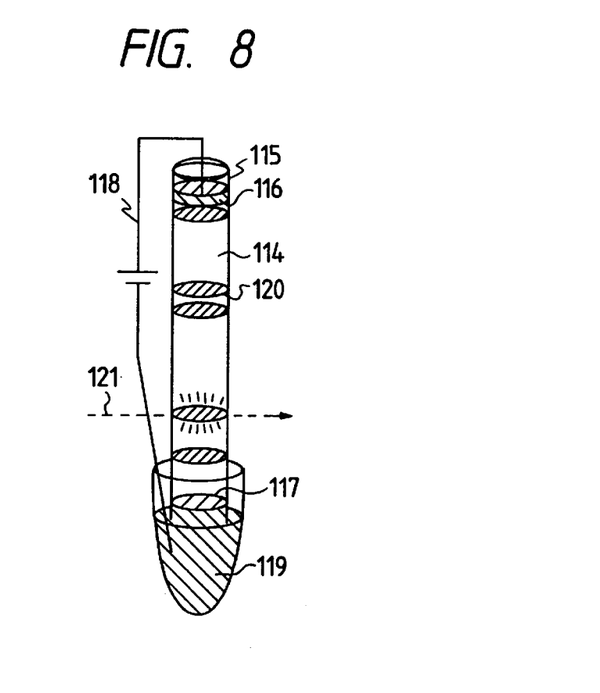
FIG. 8 is a schematic illustration to show the DNA fragment separation and individual DNA separation taking method in another embodiment of the present invention.

The generated DNA fragment group is separated and taken out by electrophoresis using gel 114 whenever required, as shown in FIG. 8. According to the present embodiment, acrylamide gel of 8 percent T (total acrylamide concentration) and 3 percent C (concentration of chemical agent for cross link) filled in the glass tube 115 having an inner diameter of 2 mm was used in the separating portion. Shorter DNA fragments 120 move faster, so they are taken separately from the shorter fragments into the container 119 sequentially. Laser 121 having irradiated on a specified position in the glass tube excites the labeled fluorophore 104, when the DNA fragment has passed by. This makes it possible to estimate the length of the DNA fragments previously separated by monitoring the fluorescent light emitted from the migrating DNA, as well as the number of fragments in the mixture. The fractionation of DNA fragments utilizes the difference between the molecular weights of DNA fragments or the specificity of the base sequence. When the PCR operation is to be performed, this operation of fractionation provides effective pretreatment. PCR is performed in order to get the amount of nucleic acids required for the base sequencing operation.

Figure 9:
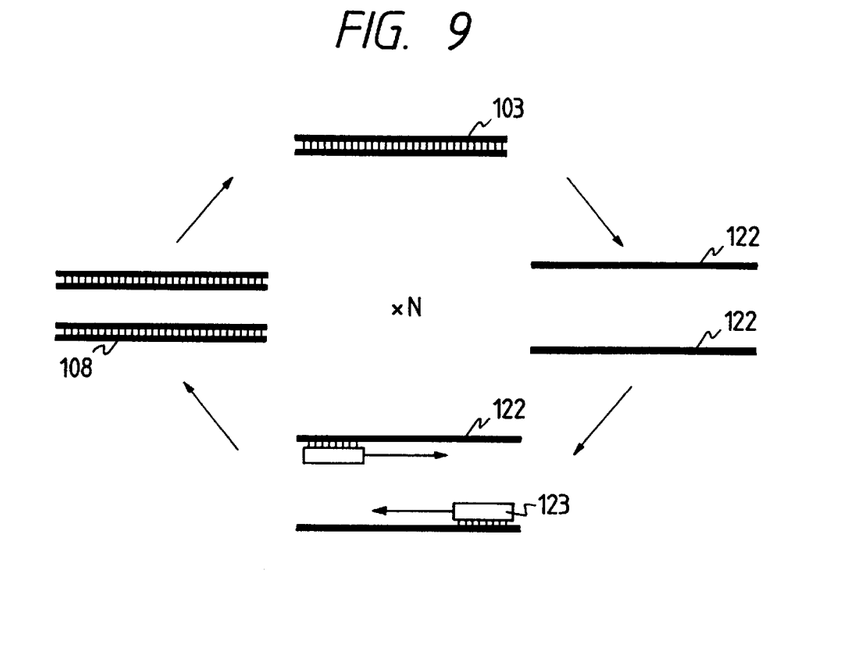
FIG. 9 is a schematic illustration to show the DNA fragment amplification procedure using PCR (Polymerase Chain Reaction) process.

PCR provides a method of amplifying the copy number of original DNA fragments 103 enzymatically, as shown in FIG. 9. The DNA fragments 106 digested by restriction enzyme (Hind III) 102 and fractionated are denatured to single stranded DNA 122 by increase in temperature. Since the sequence on each 3' terminal side is the known sequence, DNA strand (primer) 123 which can be bonded thereto is hybridized by reducing the temperature. With primer 123 as the starting point, each complementary strand is synthesized, and the copy 108 of original DNA is generated. The DNA strand generated is dissociated into one strand by raising the temperature again. When this cycle is repeated n-times, the DNA copy number is amplified to 2 raised to n-th power.

Five to six types of DNA fragments 107 are obtained in a great amount by such a method; of them, only one type is selected by the selective base sequencing method shown in FIGS. 10A and 10B, resulting in determination of the base sequence. DNA fragment group 107 including five to six fragment species as shown in FIG. 6. The fragments have the known sequence portion comprising the portion digested by restriction enzyme on both terminals and oligomer connected thereto, and the unknown sequence portion between them.

This DNA is made into the single stranded DNA 109 or 111 as shown in FIGS. 10A and 10B; then this is hybridized with the primer 110 comprising the base sequence complementary with the base sequence, which is composed of said known sequence portion and two bases on the 3' terminal side of its ensuing unknown sequence portion. The two bases on the 3' terminal side of the DNA fragment correspond to the unknown sequence, and the type of the base sequence varies depending on the DNA fragment species. Therefore, the type of the primer which perfectly hybridizes to each of them varies depending on the DNA fragment species. FIG. 10A shows the case of perfect hybridization with DNA fragment 109, whereas FIG. 10B shows the case of an imperfect hybridization with DNA fragment 111. Namely, FIG. 10A shows the case where complementary DNA strand extension reaction takes place, but FIG. 10B shows the case where complementary DNA strand extension reaction does not proceed. Thus, of DNA segment group 107 comprising five to six species, only one type of DNA fragments (maybe more than one species depending on the case, where selective sequence must be increased from 2 to 3) can selectively determine the base sequence.

Figure 11:
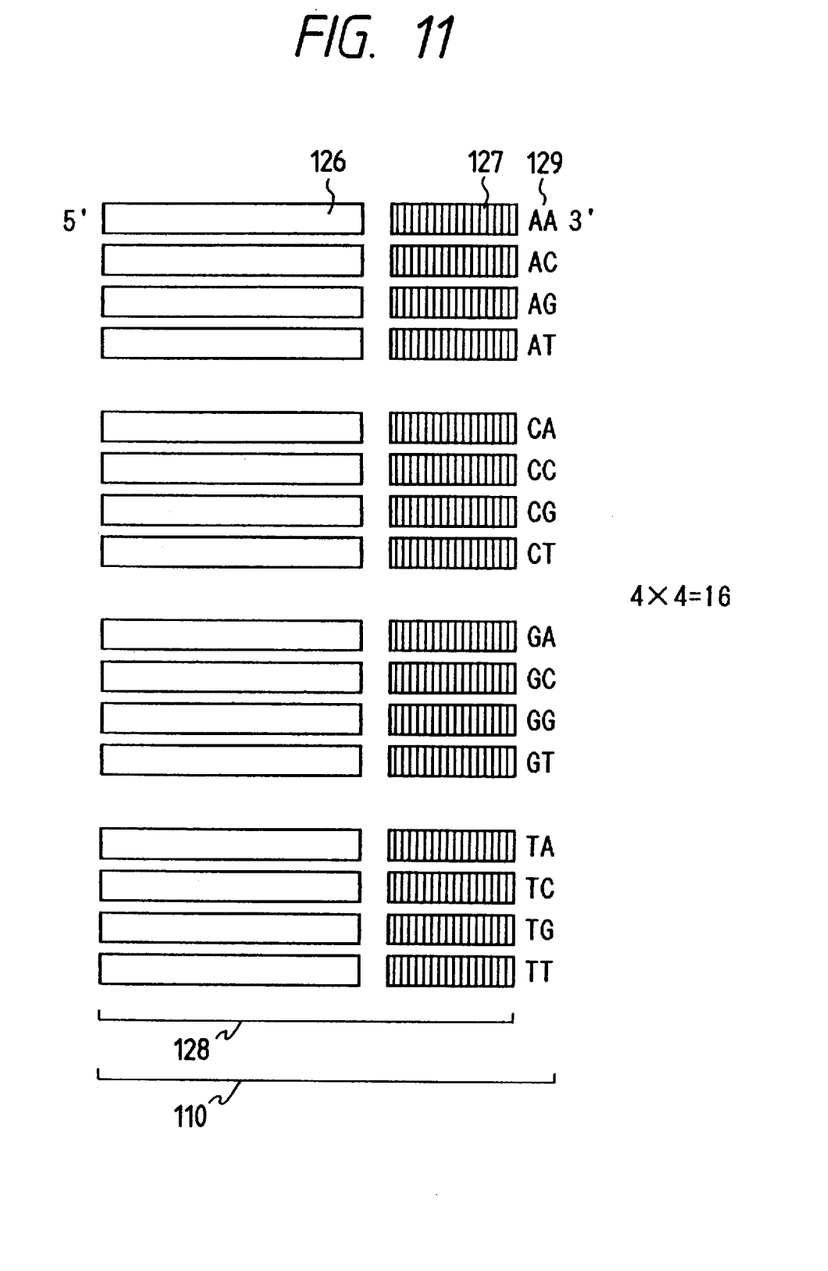
FIG. 11 is a diagram representing the base sequence of the primer used in selective base sequencing in another embodiment of the present invention.

Regarding the structure of the primer required for this selective base sequencing operation, FIG. 11 shows the case where there are two DNA fragment species in a group which have the same sequence of the 3' terminal of an unknown sequence portion, for example. The portion 128 in the primer, which is hybridized with the known sequence portion of the 3' terminal of the DNA fragment, comprises the portion 126, which is hybridized with the known sequence newly bonded by ligation or the like, and portion 127 which is hybridized with a sequence recognized by a restriction enzyme. The 3' terminal side of the primer which immediately adjacent the known sequence region hybridizes with the unknown sequence portion of DNA fragment, so four types of the first base and four types of the second base (4×4=16), namely, sixteen types, are prepared to cover all cases. This is used not only for base sequencing but also for amplification of only specific fragments during PCR amplification.

Since hybridization between said primer and DNA fragment is attributable to hydrogen bonding, hybridization is stabilized at the 3' terminal portion only when these hybridizations have perfectly matched sequence if hybridization temperature is raised. Therefore, if hybridization reaction temperature (annealing temperature) is set to 60 degrees Celsius or more, more effective selection will be made, resulting enhanced selectivity.

Making DNA have the known sequence portion and the unknown sequence portion and using the selection primer according to the above principle, we performed base sequencing operation as described below.

In the presence of 10 mM Tris-HCl, pH 8.5, 6 mM $MgCl_2$, 1 pmol of primer, 0.45 pmol of sample DNA and 1 unit of AMPLITAQ® DNA polymerase, a thermostable enzyme, are mixed together to obtain a final volume of 15 µl. ddATP as a terminator is added to dATP, dCTP, dGTP and dTTP as the DNA solution in a sample tube with 0.5 ml volume to get a total of 1 µl then dispensed into the "A-reaction tube". The A-reaction tube thus prepared, "C-reaction tube" containing ddCTP instead of ddATP, "G-reaction tube" containing ddGTP and "T-reaction tube" containing ddTTP are prepared in advance. 3.5 µl of the mixed solution of the primer and sample is dispensed into each of the A, C, G and T tubes. Furthermore, 1 to 2 drops of mineral oil are put into them, and the tubes are placed in a DNA thermal cycler. For cycle reaction conditions, temperatures of 95 degrees Celsius for 30 seconds and 72 degrees Celsius for one minute are repeated in the case of the cycle time being 1 to 15 cycles. In the case of 15 to 30, temperatures of 95 degrees Celsius for 30 seconds and 72 degrees Celsius for one minute are repeated. DNA complementary strand extension reaction is carried out by this cyclic reaction, thereby generating DNA fragments where 3' termini are ddATP from "A reaction", ddCTP from "C reaction" and so on. After completion of cyclic reaction, 2 µl of formamide, reaction stop solution, is added, and the reaction mixtures are loaded on the gel which is set in the fluorescent DNA sequencer. 1,400-volt voltage is applied to a 40 cm gel to separate the DNA fragment and to determine its base sequence.

In this case, a hybridized reaction temperature (annealing temperature) is set at 60 degrees Celsius or more; the Taq cycle sequencing was performed using Taq polymerase thermostable enzyme. Other thermostable enzymes can be used. Depending on number of fragment species in a sample, selective hybridization may be performed without setting the hybridized reaction temperature (annealing temperature) to 60 degrees Celsius or more. In such cases, base sequencing operations can be performed using a polymerase which is not a thermostable enzyme. Selective base sequencing operation can be performed using the dideoxynucleotide sequencing method where reactions are carried out by labeling the terminator nucleotide (ddNTP) if the primer is not labeled.

In the above drawing, numeral 105 denotes the DNA fragment group digested by a restriction enzyme and labeled with a fluorophore, numeral 116 the upper buffer cell, numeral 117 the lower buffer cell, numeral 118 the electrode' numeral 124 the known sequence on the 5' terminal side of single stranded DNA fragment, numeral 125 the known sequence on the 3' terminal side of single stranded DNA fragment, and numeral 129 the known sequence portion and two- to six-base portion bonded to the unknown sequence portion bonded to the 3' terminal side following it.

The present invention permits simple base sequencing without requiring any specific facility such as a P2 facility for cloning of target DNA. It does not require culturing of bacteria, so base sequencing, including sample preparation, can be completed in a shorter period of time. Furthermore, this method allows all operations to be done in test tubes, encouraging automation of the operation process. According to the present invention, furthermore, a long DNA segment is digested and separated to identify the sequence at both terminals of the digested and separated DNA, and each fragment can be separated by hybridization. This method further allows DNA analysis in a short time by simultaneous analysis of the separated fragments. For example, if the DNA of 1 mega base is separated into 500 fragments having an average strand length of about 2 Kb and is analyzed in parallel, then terminal sequence search and separation can be completed in two or three days; sequencing can be completed in three or four days by using gel capillary arrays and primer walking. So analysis is completed in about one week, thereby allowing analysis to be made 100 times faster than when using the conventional method.

---

What is claimed is:

1. A DNA analyzing and classifying method comprising:

i) digesting a double stranded DNA with a restriction enzyme to produce DNA fragments, ii) ligating a double stranded oligomer having a known base sequence to termini of the DNA fragments, iii) hybridizing primers to the DNA fragments ligated to the oligomer, under conditions sufficient to allow hybridization,     wherein said primers comprise sixteen different primers each having a known base sequence identical in all the primers and two bases directly adjacent to the known base sequence at the 3' terminus of each of the primers,     wherein sequences of the two bases are selected from the group consisting AA, AT, AC, AG, TA, TT, TC, TG, CA, CT, CC, CG, GA, GT, GC and GG, and     wherein the known base sequence of each of the primers includes a base sequence which can be hybridized with at least a part of the oligomer ligated to termini of the DNA fragments and has a recognition sequence for the restriction enzyme in the DNA fragments ligated by the DNA oligomer, iv) extending the primer hybridized with the DNA fragments ligated to the oligomer to synthesize DNA complementary to the strands of the DNA fragments ligated to the oligomer, and v) analyzing products from step iv) and classifying the DNA fragments ligated to the oligomer based upon which primers are extended,     wherein the DNA fragments ligated to the oligomer are classified by a difference in a sequence of two bases directly adjacent to the recognition sequence in the DNA fragments ligated to the oligomer.

2. A reagent kit for selecting or identifying DNA fragments comprising:

sixteen different primers each having a known base sequence identical in all the primers and having two bases directly adjacent to the known base sequence at the 3' terminus of each of the primers, wherein the sequence of the two bases is selected from the group consisting of AA, AT, AC, AG, TA, TT, TC, TG, CA, CT, CC, CG, GA, GT, GC AND GG, wherein the known base sequence of each of the primers includes a base sequence which can be hybridized with at least a part of an oligomer ligated to termini of a composition of DNA fragments and with a recognition sequence for a restriction enzyme in the DNA fragments ligated to the oligomer.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

TGTAAAACGA CGGCCAGTG 19

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:2:

AATTCACTGG CCGTCGTTTT ACA 23

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:3:

GAATTCACTG GCCGTCGTTT TACA 24

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:4:

TGTAAAACGA CGGCCAGTGA ATTC 24

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO (xi) SEQUENCE DESCRIPTION: SEQ ID NO:5:

NGAATTCACT GGCCGTCGTT TTACA                                                             25

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iv) ANTI-SENSE: NO

(xi) SEQUENCE DESCRIPTION: SEQ ID NO:6:

GACGGCCAGT GAATTCN                                                                       17

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iv) ANTI-SENSE: NO

(xi) SEQUENCE DESCRIPTION: SEQ ID NO:7:

GACGGCCAGT GGATCCN                                                                       17